US009078735B2

(12) United States Patent
Perkins

(10) Patent No.: US 9,078,735 B2
(45) Date of Patent: Jul. 14, 2015

(54) ANKLE-FOOT ORTHOTIC DEVICE

(71) Applicant: Dale Perkins, Boise, ID (US)

(72) Inventor: Dale Perkins, Boise, ID (US)

(73) Assignee: COYOTE DESIGN & MANUFACTURING, INC, Boise, ID (US)

( * ) Notice: Subject to any disclaimer, the term of this patent is extended or adjusted under 35 U.S.C. 154(b) by 196 days.

(21) Appl. No.: 13/750,948

(22) Filed: Jan. 25, 2013

(65) Prior Publication Data

US 2014/0039368 A1 Feb. 6, 2014

Related U.S. Application Data

(60) Provisional application No. 61/590,810, filed on Jan. 25, 2012.

(51) Int. Cl.
*A61F 5/00* (2006.01)
*A61F 5/01* (2006.01)

(52) U.S. Cl.
CPC .................. *A61F 5/0111* (2013.01)

(58) Field of Classification Search
CPC ... A61F 5/0111; A61F 5/0123; A61F 5/0127; A61F 5/01; A61F 2005/0165; A61F 5/0118; A61F 5/0106; A61F 2005/0181; A61F 5/012; A61F 5/0102; A61F 5/0125; A61F 5/0104; A61F 5/0109; A61F 5/0195; A61F 5/0167; A61F 5/0172
USPC ............ 602/5, 12, 16, 20–28; 128/882; 5/624
See application file for complete search history.

(56) References Cited

U.S. PATENT DOCUMENTS

| 487,492 | A | * | 12/1892 | Pugley ............................ 602/65 |
| 4,280,489 | A | * | 7/1981 | Johnson, Jr. .................... 602/27 |
| 4,938,777 | A | | 7/1990 | Mason et al. |
| 5,088,480 | A | | 2/1992 | Wang |
| 5,125,400 | A | * | 6/1992 | Johnson, Jr. .................... 602/13 |
| 5,501,659 | A | * | 3/1996 | Morris et al. ................... 602/27 |

(Continued)

OTHER PUBLICATIONS

Acor C.R.O.W. Boot, Acor®, http://www.acor.com/, at least as early as 2011.

(Continued)

*Primary Examiner* — Michael Brown
(74) *Attorney, Agent, or Firm* — Pedersen and Company, PLLC; Ken J. Pedersen; Barbara S. Pedersen

(57) ABSTRACT

An external orthotic device increases comfort, stability, and motion control of the ankle and/or foot. An outer shell comprises separate medial and lateral portions, attached to each other only by a flexible/hinge connector that extends between and is preferably anchored to each of the portions in an under-the-foot region of the shell. This connector retains the bottom end of the shell portions together, but allows the shell portions to pivot or otherwise move relative to each other with the bottom-of-the-foot connector as the pivot axis. This pivoting allows the shell to open wide for donning and doffing of the orthotic device and for adjusting the closeness of the two portions to tighten the two portions on the wearer. Strap(s) or other retainer may tighten the medial and lateral portions together around a liner into which the wearer inserts his/her foot.

18 Claims, 6 Drawing Sheets

(56) References Cited

U.S. PATENT DOCUMENTS

| | | |
|---|---|---|
| 6,503,178 B1 | 1/2003 | Gibbons |
| 6,676,618 B2 | 1/2004 | Andersen |
| 7,740,602 B2 | 6/2010 | Christensen |
| 7,931,567 B2 | 4/2011 | Rosenberg et al. |
| 8,366,591 B2 | 2/2013 | Patoglu |
| 2003/0153852 A1 | 8/2003 | Hinshon |
| 2012/0271214 A1 | 10/2012 | Blanck |
| 2013/0165833 A1 | 6/2013 | Blanck |
| 2013/0267878 A1 | 10/2013 | Franke et al. |

OTHER PUBLICATIONS

Example of prior art, Ankle-foot orthotic boot, http://wedemeyerchiropractic.com/images/afo.jpg, at least as early as 2011.

Ankle-foot orthosis (AFOs), Orthotics—Wikipedia, the free encyclopedia, http://webcache.googleusercontent.com/search?q=cache:tEtwfLHu_jUJ:en.wikipedia.org/ . . . , Jun. 22, 2011.

* cited by examiner

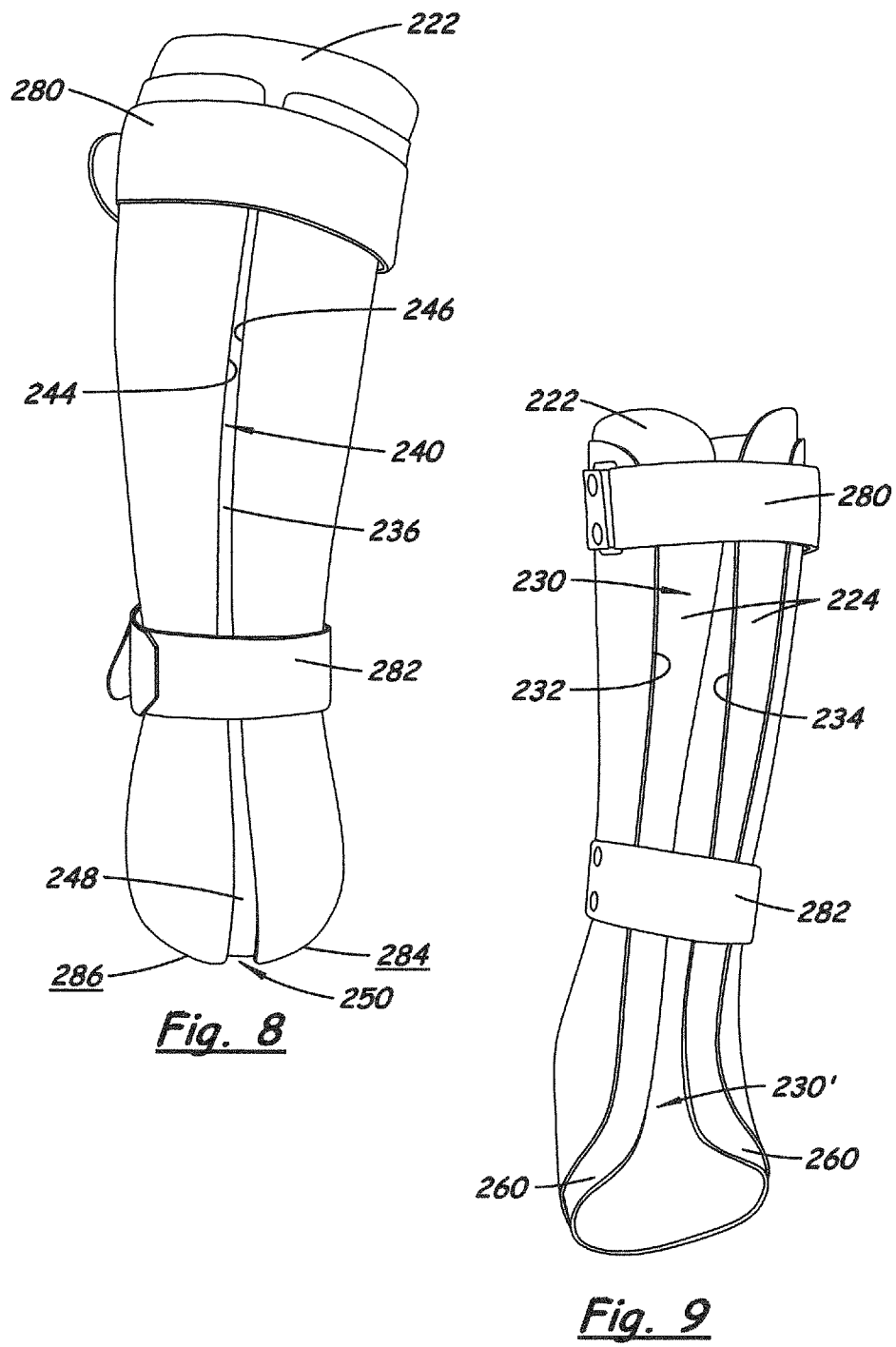

ANKLE-FOOT ORTHOTIC DEVICE

This application claims benefit of Provisional Application 61/590,810, filed Jan. 25, 2012, the disclosure of which is incorporated herein by this reference.

BACKGROUND

1. Field of the Invention

The disclosed device is a lower limb orthotic device, and more specifically, an ankle-foot orthosis (AFO). AFOs are conventionally designed to encompass the ankle joint and part or all of the foot. AFOs are externally-applied and intended to control position and motion of the ankle, for example, to compensate for weakness and/or correct deformities. AFOs are commonly used in the treatment of disorders affecting muscle function, such as stroke, spinal cord injury, muscular dystrophy, cerebral palsy, polio, MS, and/or peripheral neuropathy.

2. Related Art

Two examples of conventional AFOs are shown in FIGS. 1-4. One may note that these conventional AFOs comprise a wrap that extends continuously around the posterior of the ankle and lower leg, and continuously under the foot, with no gap/slit at or near said posterior or said bottom. FIGS. 1 and 2 illustrate a conventional AFO that may be likened to a wrap-around boot of flexible leather, plastic or fabric, laced like a shoe and having straps at or above the ankle. FIGS. 3 and 4 illustrate an AFO such as the C.R.O.W. (Charcot Restraint Orthotic Walker)™ by ACOR®, having an outer shell and an inner liner, both extending continuously around the posterior of the foot and ankle, and continuously around the bottom of the foot.

SUMMARY

The invented device comprises an external orthotic device for a wearer to use on his/her lower leg, to increase comfort, stability, and motion control of the ankle and/or foot. The device comprises a multiple-portion outer shell that may be tightened around an inner liner into which the foot and ankle are inserted. In certain embodiments, the inner liner is a single piece that wraps around the lower leg and foot and that is open at the front of the leg, top of the foot, and toe. Tightening the preferred multiple-portion outer shell around the inner liner comprises the portions of the shell moving closer together at the posterior as well as at the anterior of the leg, and at the bottom as well as at the top of the foot. Thus, the multiple-portion shell is adapted to provide more uniform and effective support to the ankle and foot, compared to prior art orthotics that are continuous around the rear of the leg/ankle and the bottom of the foot.

Certain embodiments of the outer shell comprise two portions, a medial portion and a lateral portion, which are entirely or substantially separate but are held together, and tightened, around the lower leg by one or more straps, cinches, ties or other fasteners that pull the two separate portions together. Certain embodiments comprise one or more flexible/hinge connector(s) that extend(s) between the portions and is/are preferably anchored to each of the portions in an under-the-foot region of the shell, and, hence, these embodiments are examples of substantially (rather than entirely) separate medial and lateral shell portions. Such a connector retains the bottom end of the shell portions together, but allows the shell portions to pivot or otherwise move relative to each other, for example, by the connector flexing, bending, or pivoting in a hinge-like fashion. This flexible/hinge connection between the bottom end of the shell portions results in said shell portions being moveable relative to each other along all of the length of the shell. This relative movement may comprise the two portions pivoting relative to each other, with the flexible/hinge connector comprising a pivot-axis. This pivoting may allow, for example, the shell to open wide in a clam-shell manner for donning and doffing of the orthotic device and for adjusting the closeness of the two portions to tighten the two portions on the wearer, preferably with a liner in between the shell and the wearer.

The medial and lateral portions of the shell may be connected to each other along a short distance, for example, along a portion of the bottom of the shell, preferably underneath the foot in the area of the arch. In certain embodiments, this is the only connection between the two shell portions at the bottom region of the device, and is the only connection between the two shell portions at any region of the device other than one or more adjustable straps or closures encircling the device at and/or above the ankle. The connection is preferably provided by a flexible or otherwise moveable connector, to provide a hinge function so that the medial and lateral portions may be moved apart, for donning and doffing the device, and for adjustably tightening the two portions on the wearer. In certain embodiments, the two portions and the connector are sized, shaped and/or oriented so that the edges of the two portions are spaced apart all along said edges during use. Therefore, this may result in there being a gap/space between the medial and lateral portions all along the posterior and bottom of the device, from the top edge of the device, down the posterior of the leg and heel, and forward all along the length of the foot to the forward-most edge of the device. Thus, even when the two portions are tightened significantly, it is usually preferred that the gap/space exist between the edges of the two shell portions, both along the posterior, the bottom, and the front of the device. In certain embodiments, the two portions may be tightened to such an extent that the edges of the front or rear touch or overlap, for example, but it is preferred that the device be custom-manufactured to be custom-fit to the wearer so that there are gaps/spaces between all edges of the two portions even when fully-tightened on the wearer.

The two shell portions are preferably fabricated of material(s) that is/are rigid but not brittle. For example, the shell portions may comprise a composite fabric or "laminate" comprising basalt fibers (basalt fabrid), but may alternatively comprise fiberglass (E-glass and/or S-glass for example), ultra-high-molecular weight polyethylene fabrics (such as "spectra cloth"), Kevlar™, "ballistics fabrics", carbon fiber, and/or nylon fabrics, for example. It is preferred to use materials that are rigid or substantially rigid, so that the force applied to pull or hold the two portions of the shell together are evenly applied through the shell, and, hence, along the entire covered surface of the liner. It is especially preferred that the shell not be brittle, because the heal strike force on the shell during walking may be substantial, and it is important for the shell portions not to break or crack.

Between the shell and the wearer (or his/her stocking or other skin-cover if used) is received a device liner. The liner is preferably a semi-rigid but flexible (or "somewhat flexible") plastic wrap/cover that provides a comfortable, total-contact interface between the liner and the wearer's lower leg (typically the ankle and foot, and few inches of leg above the ankle but below the knee). The liner, unlike the shell, is preferably continuous or substantially continuous around the posterior and the bottom of the device, so that the liner extends continuously around the back of the wearer's leg, along the heel, and underneath the foot. The preferred device, therefore, comprises a liner that is generally continuous around the foot and ankle, except for the top opening through which the leg extends, the toe opening, and the longitudinal opening/slit along the anterior region of the foot and leg.

The shell is easily donned around the liner, due to the flexible/hinge connector, and the two shell portions may be "cinched" together by use of straps (or other ties, tethers, buckles, or cinches) a desired amount around the liner and limb. This cinching moves the two shell portions inward toward each other both at the posterior and the anterior of the device/leg. In other words, the medial and lateral portions may be cinched together a desired amount to move all or substantially all of the edges of said portions toward each other, that is, posterior edges, bottom edges, and anterior edges. Preferably, all of the posterior edges and all of the anterior edges will move closer together. All or substantially all of the bottom edges may also move closer together, for example, preferably all of the bottom edges minus the portion (the "connector-portion") of the bottom edges wherein a connector between the edges prevents significant closure of the gap/space.

The cinching or other tightening of the two shell portions applies consistent and controllable pressure on the entire or substantially the entire liner, which in turn presses consistently and controllably on the entire or substantially the entire lower leg, ankle and foot of the wearer. Thus, contact and pressure may be supplied firmly, controllably, and comfortably to at least the entire ankle and foot area (except the exposed toe region). This results in better control, stability, and comfort during use, compared to prior art devices in which the boot/shell is a one-piece unit without any space/gap at the back or bottom of the leg, ankle, and foot.

These and/or other objects, structures, functions and/or methods of construction and use of the disclosed device will be apparent from the Figures and the Detailed Description below.

BRIEF DESCRIPTION OF THE DRAWINGS

FIGS. 8 and 9 are posterior and anterior views, respectively, of the device of FIG. 5.

DETAILED DESCRIPTION

Referring to the figures, there are shown several prior art ankle-foot orthotic devices (AFOs), in FIGS. 1-4, and one, but not the only, embodiment of the disclosed ankle-foot orthotic device 10 or "walking orthosis" (FIGS. 5-12).

Figures 1, 2:
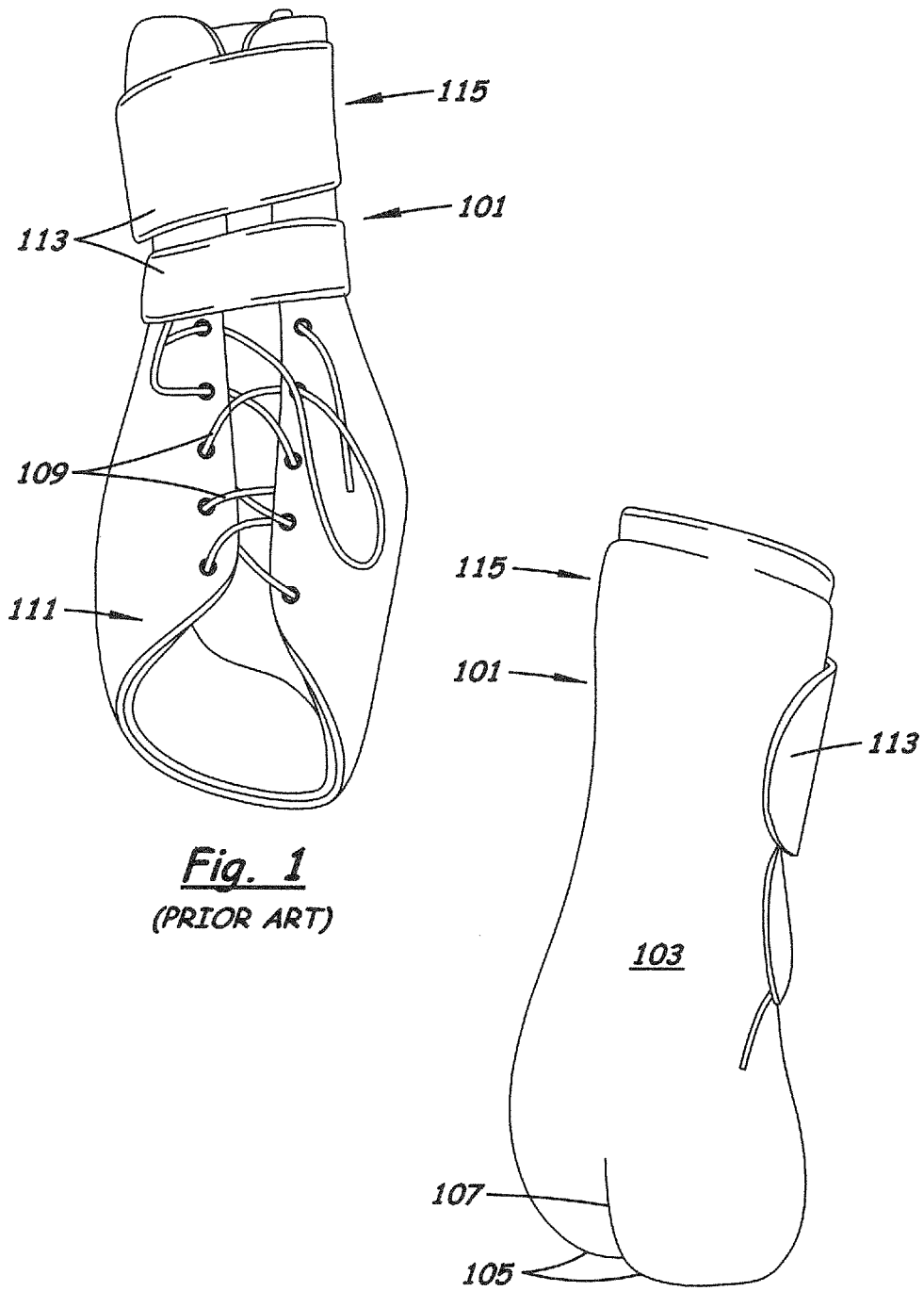
FIGS. 1 and 2 are anterior (front) and posterior (rear) views, respectively, of a prior art AFO lace-up boot device.

FIGS. 1 and 2 are anterior (front) and posterior (rear) views, respectively, of a prior art AFO lace-up boot device 101. Note that the boot body is one-piece, and the rear surface 103 does not comprise any gap/space (FIG. 2) and the bottom surface 105 (bottom of foot region 111) does not comprise any gap/space. This boot body is continuous around the rear of the leg, ankle, and underneath the foot, and only opens at the top and front of the device 101. There may be some indentations/curvature 107 at the rear or bottom, but there are no spaces/gaps in the rear and bottom walls of the boot body. Laces 109 are provided to tighten the foot region 111 of the device. Hook-and-loop-fastener flaps 113 are provided at the ankle and/or lower leg region 115 of the device.

Figures 3, 4:
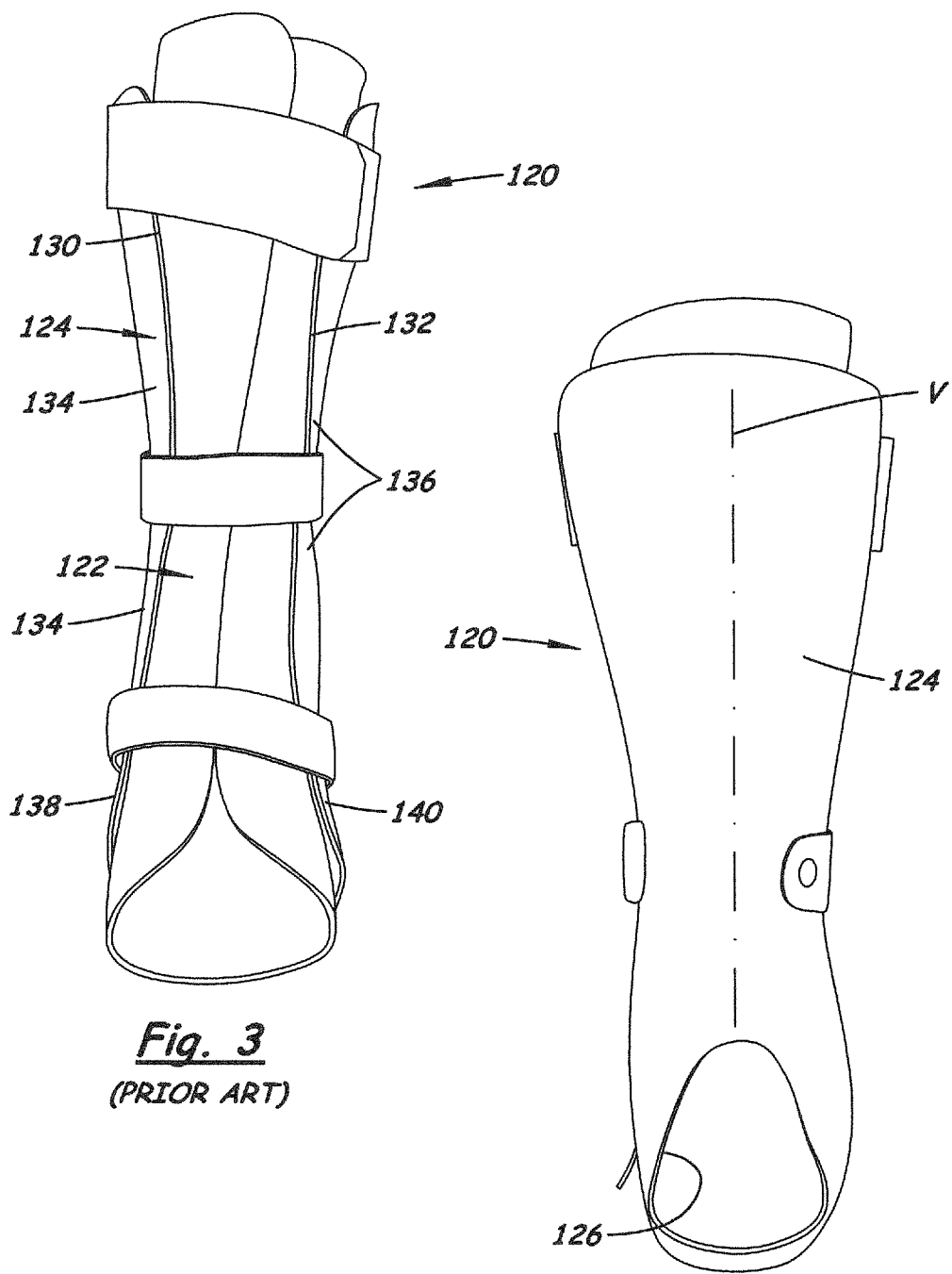
FIGS. 3 and 4 are anterior (front) and posterior (rear) views, respectively, of a prior art AFO C.R.O.W.™ device.

FIGS. 3 and 4 are anterior (front) and posterior (rear) views, respectively, of a prior art AFO C.R.O.W.™ device 120. Note that this device 120 comprises a liner 122 and a one-piece shell 124, wherein there is no space/gap at the rear or bottom of the shell, except that non-moveable holes (for example, hole 126 for the heel) may be present. "Non-moveable" here means that no portion of the shell around the hole will move relative to any other portion of the shell around the hole. In other words, the shell of this device shown in FIGS. 3 and 4 is continuous around the rear of the leg, ankle, and underneath the foot, except for a hole for the heel. This device 120 may comprise straps 128 that pull the front edges 130, 132 of the shell 124 together, thus, tightening the shell by pulling only the forward (anterior) leg regions 134 and 136 and the forward/top foot regions 138 and 140) of the shell toward each other.

Figures 5, 6:
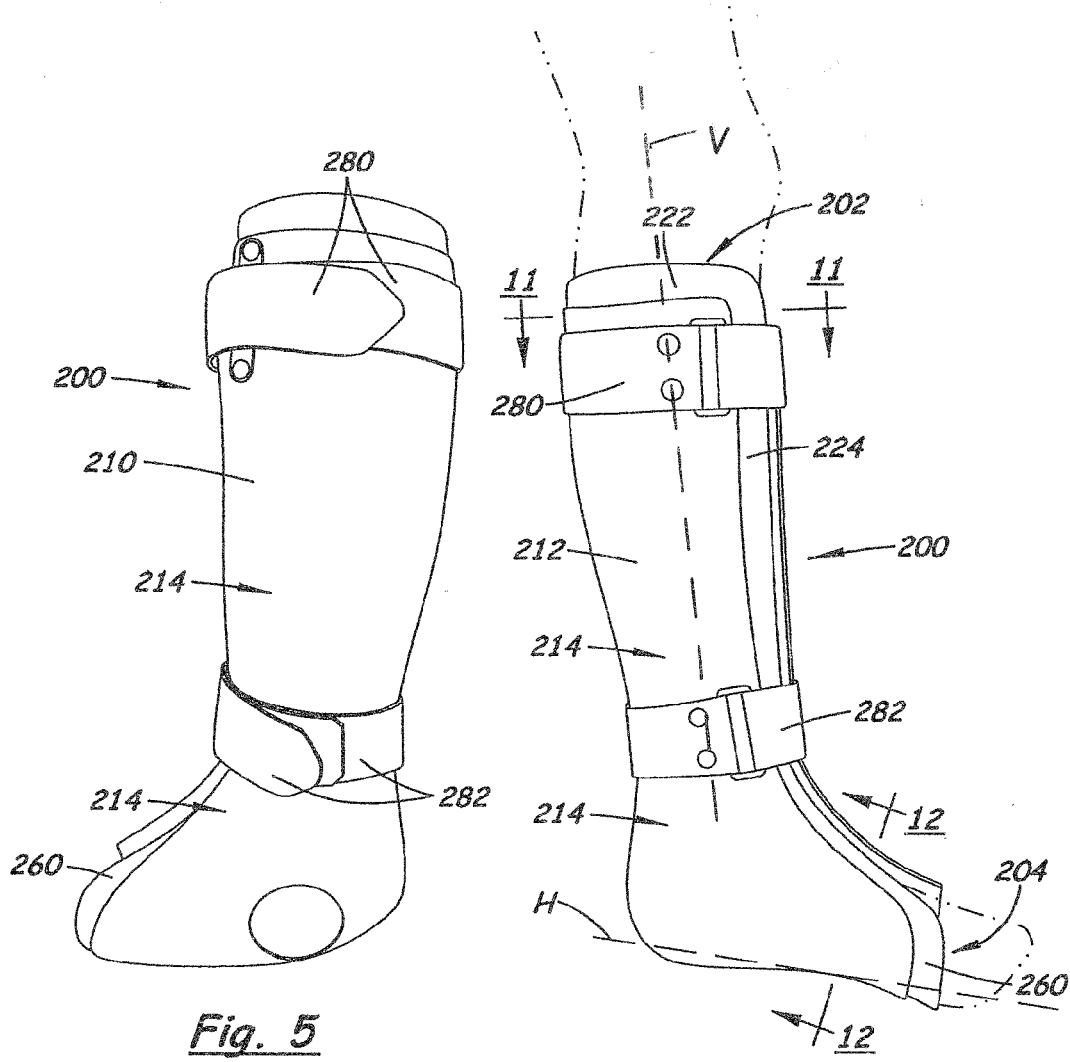
FIG. 5 is a lateral side view of one embodiment of the ankle-foot orthotic device, positioned as it would appear installed on a wearer.
FIG. 6 is a medial side view of the embodiment of FIG. 5. Note the dashed-line knee and upper leg, and toes, of a wearer in FIG. 6.
Figure 7:
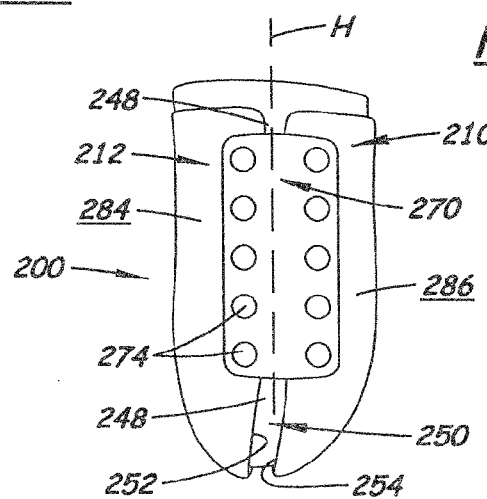
FIG. 7 is a bottom view of the foot-region of the device of FIG. 5.

FIGS. 5 and 6 are a lateral side view, and medial side view, respectively, of one embodiment of the invented device 200, positioned as it would appear when installed on a wearer. FIGS. 8 and 9 are a posterior and an anterior view, respectively, of the device 200. FIG. 7 is a bottom view of the device. Note the dashed-line knee and upper leg extending through the top opening 202 of the device 200, and the toes of a wearer extending through the toe opening 204, in FIG. 6.

The two shell portions 210, 212 are generally halves of the shell 214. A liner 220 is inside, and substantially enveloped by, the shell 214. The liner 220 as a whole is shown and called-out in FIG. 10, whereas its visible portions are shown and called out in FIGS. 5-9. Because the shell 214 covers most of the liner 220 in the in-use figures (FIGS. 5-9), only small portions of the liner 220 are visible, specifically, top edge area 222 extending through top opening 202 (FIGS. 6, 8 and 9), front area 224 showing in the gap 230 between the front edges 232, 234 of the shell 214 (FIGS. 6 and 9), rear area 236 showing in the gap 240 between the rear edges 244, 246 of the shell 214 (FIG. 8), bottom area 248 showing in the gap 250 between the bottom edges 252, 254 of the shell 214 (FIGS. 7 and 8), and toe area 260 extending through toe opening 204 (FIGS. 5, 6 and 9).

Figure 10:
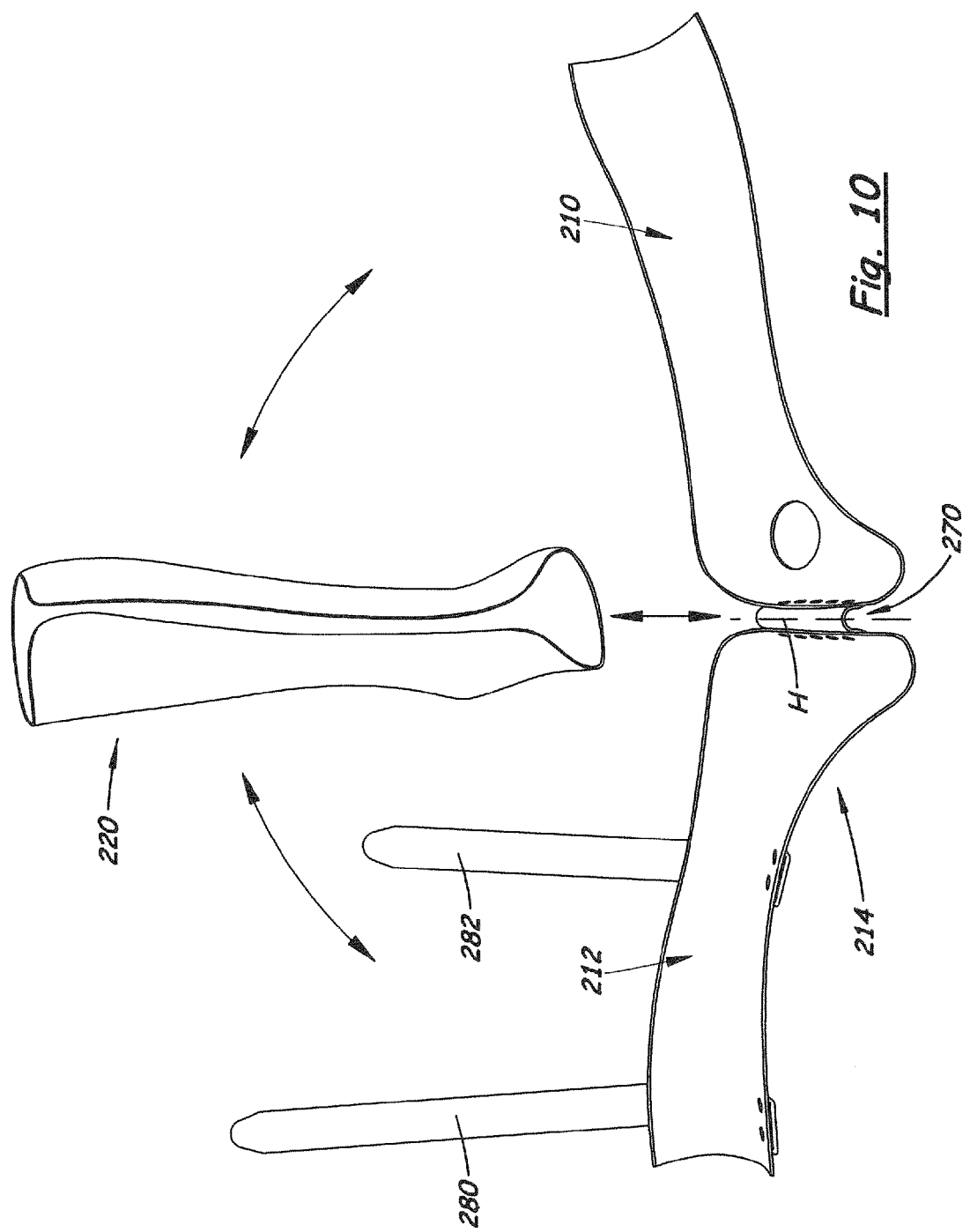
FIG. 10 is a front view of the device of FIG. 5, wherein the shell portions are pivoted apart and separated from the liner.

In the bottom view of FIG. 7 may be seen one embodiment of a flexible/hinge connector 270 that extends between and moveably connects the lateral portion 210 ("lateral half") and the medial portion 212 (medial half) of the shell. The connector 270 comprises a strap/tab 272 that extends between and overlaps the two shell portions 210, 212 and is fastened to said portions 210, 212 by various means, for example, rivets 274. As shown in FIG. 10, which is discussed further below, the connector 270 is flexible or bendable (hence, a "hinge" function) to allow the two shell portions 210, 212 to pivot relative to each other to be distant at their top ends. It is preferred that a single connector be used, but multiple, smaller connectors may be used at the bottom of the foot end of the shell. Other embodiments of connector(s) may be used at the bottom of the foot end of the shell, for example, latches, ties, and/or cords, hinges, with the connector(s) preferably being generally flat in order to not cause discomfort when walking in the device 200 alone or in the device covered by footwear or other utilitarian or aesthetic coverings.

In certain embodiments, one or more connectors (such as connector 270) is/are the only connectors directly connecting/attaching the two shell portions 210, 212 to each other. In addition to the direct connection/attachment of the two shell portions 210, 212 at the bottom end of the shell, the only other structure of certain embodiments that holds or urges the two shell portions together in use is at least one strap that wraps around the device at or near the ankle region and/or at or near the leg region of the device. Such strap(s) is/are are preferably continuously adjustable to pull (or "cinch") the two portions 210, 212 closer together. Thus, such straps do not attach the portions 210, 212 together, in that they are not fixed to both portions, but tighten around the portions during use. When removed from the wearer, such straps preferably hang from one or the other of the portions 210, 212 and do not fasten the portions 210, 212 to each other.

Examples of such straps are straps 280, 282, which are illustrated in one cinched position in FIGS. 5-9 that represents one of many amounts of tightness of the device 200 around the liner. Thus, this "one of many positions" corresponds to one of many extents to which the edges of the portions/halves (232 and 234, 244 and 246) are moved toward and held near each other to supply firm, consistent, and controlled pressure against the entire liner and covered area of the limb. In other words, the gap 240 between the posterior of the portions/halves (visible in FIG. 8) and the gap 230 between the anterior of the portions/halves (visible in FIG. 9), may be each be less, or more, than shown in FIGS. 8 and 9.

One may note that the gap 250 between the bottom edges 252, 254 will tend to stay generally the same in the embodiment drawn herein, as the connector 270 serves as the pivot axis for the pivoting of the two shell portions 210, 212 together. As the device 200 is preferably custom-fit/manufactured for the wearer, the bottom end of each of the shell portions 210, 212 (the foot of the shell), the bottom end of the liner 220, and the size of the connector 270 are sized and shaped to fit the wearer's foot, so that cinching the straps 280, 282 will result in the proper fit of the liner and shell around the foot when the two portions 210, 212 pivot together, for example, without any adjustment of the length/size/location of the connector 270 to pull the bottom surfaces 284, 286 of the shell portions together. One may understand that the edges of the bottom surfaces 284, 286 pivot toward each other during donning of the device, but that, in certain embodiments, cinching the straps 280, 282 will cause little or no further movement of said edges toward each other. In other embodiments, for example when the bottom-of-the foot connector is quite flexible/pliable, the connector may bend or compress during said cinching, allowing the edges of the bottom surfaces 284, 286 to move closer to each other in spite of the connector. Straps 280, 282 may comprise hook-and-loop fastener, such as Velcro™, or buckle fasteners and adjustable means, for example.

FIG. 10 is a front view of the device of FIGS. 5-9, wherein the shell 214 is separated from the liner 220. Note the arrows that illustrate how the two portions/halves 210, 212 of the shell 214 may be moved apart to a great extent, for example, by pivoting to lie open and flat on horizontal surface, while still preferably being connected but moveable at the flexible/hinge connector 270. Said pivoting is shown in FIG. 10 to be up to 180 degrees (from zero degrees apart in a "closed" position as in FIGS. 5-9, to 180 degrees apart in the open position of FIG. 10. Or, the shell portions and/or connector may be adapted to allow pivoting up to a greater or lesser extent, for example, an extent in the range of 10-360 degrees, 45-225 degrees, 90-180 degrees, 120-180 degrees, 150-225 degrees, or 180-225 degrees. An extent of at least 90 degrees is preferred, to provide a lot of room for the foot and liner to be inserted into the outer shell.

Figure 11:
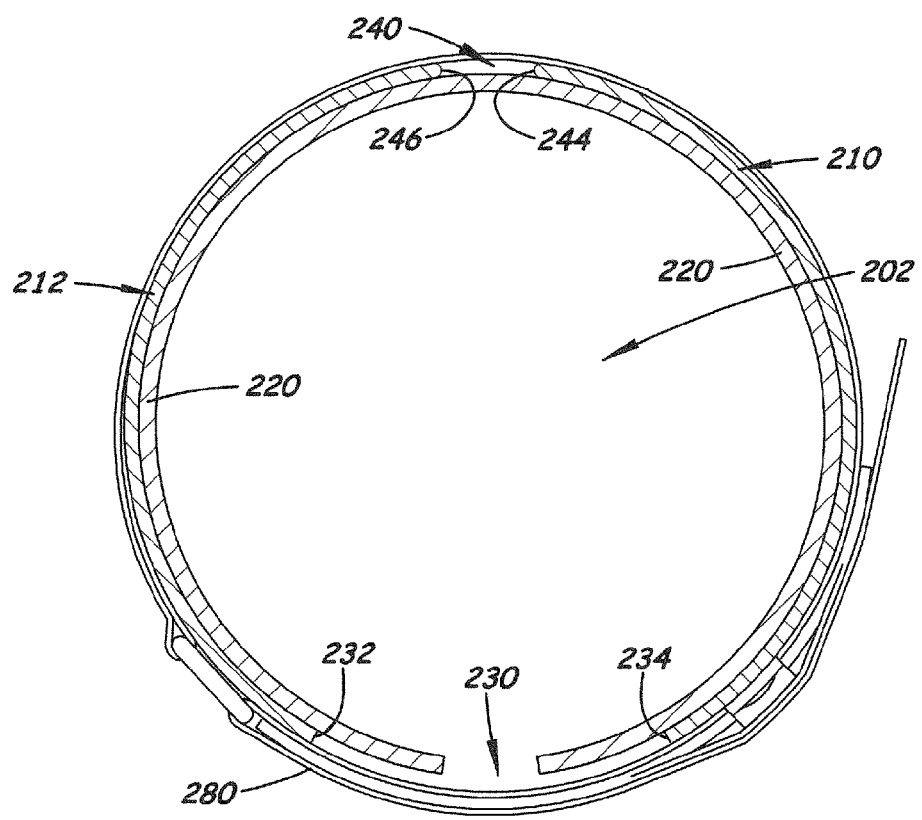
FIG. 11 is a cross-sectional view of the device of FIG. 5, viewed along line 11-11 in FIG. 6.

FIG. 11 is a cross-sectional view, along the line 11-11 in FIG. 6. Note that a space/gap is shown at both the front and the rear of the device, between the shell portions/halves, that is, gap 230 at the front and gap 240 at the rear. The strap 280 shown in this figure serves to tighten/cinch the two portions/halves 210, 212 to the desired position, at or near the top of the device.

Figure 12:
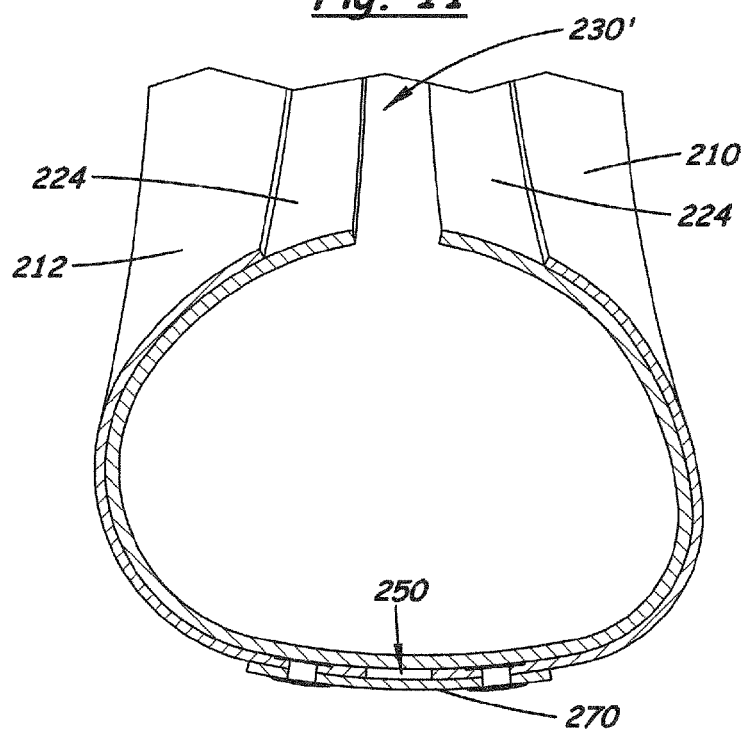
FIG. 12 is a cross-sectional view of the foot region of the device of FIG. 5, viewed along line 12-12 in FIG. 6.

FIG. 12 is a cross-sectional view of the foot region of the device, along the line 12-12 in FIG. 6. Note that a space/gap (230', that is, a lower portion of front gap 230) is shown at the top of the foot region of the shell, between the shell portions/halves. Also, a space/gap 250 is shown at the bottom of the foot region of the shell, between the shell portions/halves. The flexible/hinge connector 270 is shown extending over the bottom space/gap 250 in this view. It may be noted that there is no need, in certain embodiments, for a strap or connector (other than the flexible/hinge connector) in the foot region of the device, as the force of the ankle/leg straps holding the upper end of the device, combined with certain embodiments of connector at the bottom of the foot region, serve to retain the shell portions/halves together in the desired orientation/tightness in the foot region, as well as the ankle and leg regions.

One may note from the figures, and especially from FIG. 10, that the multiple-portion (or multiple-part) shell comprises portions pivoting on an axis at or near the bottom of the foot region of the device (and preferably generally parallel to the bottom surface of the foot region). Preferably, said axis is at or near the bottom longitudinal centerline of the wearer's foot. Thus, certain embodiments have been called by the inventor a "bivalve shell". This way, the shell portions pivot very differently and in a different direction relative to the flexing of the prior art shells, which flex at their posterior surfaces to bring the front flaps of the shell together. Certain embodiments of the disclosed shell, therefore, may be said to have portions pivoting on a horizontal axis H (horizontal or generally horizontal when in use on the standing person), while the prior art shell may, at most, flex on a vertical axis V (along the posterior, generally vertical length of the shell when in use on the standing person). One may understand from FIGS. 2 and 4, that the prior art devices comprise no adaptation for posterior tightening except that there may be some of the above-referenced flexing at the rear vertical axis V. One may also understand that making the prior art shell more rigid, to enhance support of the ankle, will typically allow the shell to flex less at axis V, resulting in an ineffective, or at best difficult, tradeoff between fit and support for such prior art devices. One may understand from FIGS. 8-12 that the preferred embodiments of the invented device comprise adaptation for tightening at the posterior as well as the anterior of the leg, and at the top of the foot and optionally at the bottom of the foot; this provides both excellent fit and support that result in excellent motion control and stability.

Certain embodiments may be described as an external orthotic device that increases comfort, stability, and motion control of the ankle and/or foot. An outer shell comprises separate medial and lateral portions, attached to each other only by a flexible/hinge connector that extends between and is preferably anchored to each of the portions in an under-the-foot region of the shell. This connector retains the bottom end of the shell portions together, but allows the shell portions to pivot or otherwise move relative to each other with the bottom-of-the-foot connector as the pivot axis. This pivoting allows the shell to open wide for donning and doffing of the orthotic device and for adjusting the closeness of the two portions to tighten the two portions on the wearer. Strap(s) or other retainer may tighten the medial and lateral portions together around a liner into which the wearer inserts his/her foot. Adjusting the multiple portions is typically done by tightening/cinching one or more straps or other fasteners around the upper region of the device, which due to the rigidity of the shell portions, tightens the entire device around the liner, and, hence, around the lower leg, foot and ankle.

Certain embodiments may be described as an orthotic device for a wearer's foot and ankle having a posterior side and anterior side, wherein the orthotic device may comprise, consist essentially of, or consist of: a multiple-piece, rigid or substantially rigid outer shell comprising a medial shell portion and a lateral shell portion, each of the shell portions having an upper end for being placed near the lower leg of a wearer, and lower end for being placed underneath the foot of the wearer, an anterior edge, and a posterior edge; a hinge-connector connecting the lower ends so that the shell portions pivot relative to each other at the hinge-connector to open the outer shell by the upper ends moving away from each other; and a fastener adapted to pull the shell portions together at the upper ends to tighten the outer shell by moving the shells together at their posterior edges and at their anterior edges. The orthotic device may also comprise a liner inside the outer shell, the liner having an anterior opening (typically all along the entire anterior length of the liner) for insertion of the wearer's foot. Each of the shell portions is preferably rigid or substantially rigid. The hinge-connector may be a flexible connector or other connector that allows pivoting of the shells on an axis parallel to the length of the foot portion of the outer shell (from toe to heel direction). The medial shell portion and the lateral shell portion are preferably only connected to each other by the hinge-connector, and may be tightened together only by the fastener, or by the fastener and also an ankle strap/fastener at a middle region of the outer shell that is adapted to tighten the outer shell by moving the shells together at their posterior edges and at their anterior edges. For example, the shell portions may be pivotable away from each other to relative positions in the range of 45-225 degrees apart. For example, the shell portions may be pivotable away from each other to at least 90 degrees apart. The fastener and said ankle-fastener may be hook-and-loop-fastener straps. In a tightened configuration on the wearer, the posterior edges of the preferred shell portions are spaced apart, and the anterior edges are spaced apart.

Certain embodiments may be described as an orthotic device for a wearer's lower leg, including the wearer's foot and ankle, the device having a posterior side and anterior side and comprising, consisting essentially of, or consisting of: multiple-piece outer shell having a foot region and a heel region, an ankle region and a calf region, the outer shell comprising two a medial shell portion and a lateral shell portion, each of the shell portions having a top end for being placed near the calf of a wearer, and a bottom end for being placed underneath the foot of the wearer, the medial shell portion and the lateral shell portion each having an anterior edge and a posterior edge; wherein the medial shell portion and lateral shell portion are connected only at their bottom regions and are pivotal on an axis extending between the toe region and the heel region of the outer shell, the shell portions being pivotal relative to each other on said axis, to distance the top ends of the shell portions to open the outer shell; and at least one fastener adapted to pull the shell portions together to tighten the outer shell by moving the shells together at their posterior edges and at their anterior edges. A liner is preferably inside the outer shell, the liner having an anterior opening, all along the length of the liner, for insertion of the wearer's foot into the liner. Each of the shell portions is preferably rigid or substantially rigid. The shell portions are preferably connected by a flexible connector or by a hinge. The medial shell portion and the lateral shell portion may be only connected to each other by the flexible connector, and are tightened together only by the said at least one fastener. Or, the medial shell portion and the lateral shell portion may be only connected to each other by the hinge, and are tightened together only by said at least one fastener. One of said at least one fastener may be an upper (calf) strap, and one of said at least one fastener may be an ankle strap, comprising hook-and-loop fastener. When the device is in a loosened configuration on the wearer, the posterior edges of the shells are spaced apart a first amount, and, when the device is in a tightened configuration, the posterior edges of the shells are spaced apart a second amount that is smaller than said first amount. When the device is in the loosened configuration on the wearer, the anterior edges of the shells are spaced apart a first amount, and, when the device is in the tightened configuration, the anterior edges of the shells are spaced apart a second amount that is smaller than said first amount. The shell portions may be described as being distanced from each other by a gap all along the length of the outer shell at the posterior side of the device. The shell portions may be described as being distanced from each other by a gap all along the length of the outer shell at the posterior side of the device and also by a gap all along the length of the outer shell at the anterior side of the device.

Although this disclosed technology has been described above with reference to particular means, materials and embodiments, it is to be understood that the disclosed technology is not limited to these disclosed particulars, but extends instead to all equivalents within the broad scope of the following claims.

The invention claimed is:
1. An ankle-foot orthotic device for a wearer's lower leg, foot, and ankle, the device having an upper end, a lower end, and posterior side and anterior side, and comprising:
   a rigid or substantially rigid multiple-piece outer shell having a foot region comprising a heel region at one end and a toe region at an opposite end, and an arch region between the heel and toe regions, and the outer shell further comprising an ankle region and a calf region, wherein the arch region extends anteriorly from the heel region to be forward relative to the ankle region and calf region, wherein the arch region is adapted to extend along the wearer's foot arch and up along sides, and across an upper surface, of the wearer's foot, and wherein the toe region is an anterior extremity of the foot region and is adapted to be near the wearer's toes, the outer shell comprising a medial shell portion and a lateral shell portion, each of the shell portions having a top end, and a bottom end, an anterior edge and a posterior edge;
   wherein the medial shell portion and lateral shell portion are connected only at their bottom ends and are pivotal relative to each other only on a single bottom longitudinal centerline axis extending between the toe region and the heel region of the outer shell foot region, to distance the top ends of the shell portions to open the outer shell; and at least one fastener adapted to pull the shell portions together to tighten the outer shell by moving the shells together at their posterior edges and at their anterior edges.

2. An ankle-foot orthotic device as in claim 1, further comprising a liner inside the outer shell, the liner having an anterior opening, all along the length of the liner, for insertion of the wearer's foot into the liner, wherein the tightened outer shell applies pressure on the entire or substantially the entire liner, which in turn presses on the entire or substantially the entire lower leg, ankle and foot of the wearer.

3. An ankle-foot orthotic device as in claim 1, wherein each of the shell portions is rigid.

4. An ankle-foot orthotic device as in claim 1, wherein the shell portions are connected by one or more flexible connectors on said single centerline axis.

5. An ankle-foot orthotic device as in claim 4, wherein the medial shell portion and the lateral shell portion are only connected to each other by the flexible connector on said single centerline axis, and are tightened together only by the said at least one fastener.

6. An ankle-foot orthotic device as in claim 1, wherein the shell portions are connected by one or more hinges on said single centerline axis.

7. An ankle-foot orthotic device as in claim 6, wherein the medial shell portion and the lateral shell portion are only connected to each other by the hinge on said single centerline axis, and are tightened together only by said at least one fastener.

8. An ankle-foot orthotic device as in claim 7, wherein each of said at least one fastener is ankle a straps comprising hook-and-loop fastener.

9. An ankle-foot orthotic device as in claim 1, wherein the shell portions are pivotable away from each other to relative positions in the range of 45-225 degrees apart.

10. An ankle-foot orthotic device as in claim 1, wherein the shell portions are pivotable away from each other to at least 90 degrees apart.

11. An ankle-foot orthotic device as in claim 1, wherein, when the device is in a loosened configuration on the wearer, the posterior edges of the shells are spaced apart a first amount, and, when the device is in a tightened configuration, the posterior edges of the shells are spaced apart a second amount that is smaller than said first amount.

12. An ankle-foot orthotic device as in claim 1, wherein, when the device is in a loosened configuration on the wearer, the anterior edges of the shells are spaced apart a first amount and the posterior edges of the shells are spaced wart a first amount, and, when the device is in a tightened configuration, the anterior edges of the shells are spaced apart a second amount that is smaller than said first amount, and the posterior edges of the shells are spaced apart a second amount that is smaller than said first amount.

13. An ankle-foot orthotic device as in claim 1, wherein the shell portions are distanced from each other by a gap all along the length of the outer shell at the posterior side of the device.

14. An ankle-foot orthotic device as in claim 1, wherein the shell portions are distanced from each other by a gap all along the length of the outer shell at the posterior side of the device and by a gap all along the length of the outer shell at the anterior side of the device.

15. An ankle-foot orthotic device as in claim 1, further comprising an ankle-fastener at a middle region of the outer shell and adapted to tighten the outer shell by moving the shells together at their posterior edges and at their anterior edges.

16. An ankle-foot orthotic device as in claim 15, wherein the medial shell portion and the lateral shell portion are only connected to each other by the hinge-connector, and are tightened together only by said fastener and said ankle-fastener.

17. An ankle-foot orthotic device as in claim 16, wherein said fastener and said ankle-fastener are hook-and-loop straps.

18. An ankle-foot orthotic device as in claim 1, wherein the calf and ankle regions have a vertical longitudinal axis and an anterior extremity, said single centerline axis is generally perpendicular to said vertical longitudinal axis, and the arch region and toe region are anterior relative to said anterior extremity of the calf and ankle regions.

* * * * *